US00PP19131P2

(12) United States Plant Patent
Zary

(10) Patent No.: US PP19,131 P2
(45) Date of Patent: Aug. 19, 2008

(54) SHRUB ROSE PLANT NAMED 'JACTOOSE'

(50) Latin Name: *Rosa hybrida*
Varietal Denomination: JACtoose

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/824,573

(22) Filed: Jun. 29, 2007

(51) Int. Cl.
*A01H 5/00* (2006.01)

(52) U.S. Cl. ..... Plt./108
(58) Field of Classification Search ..... Plt./108
See application file for complete search history.

(56) References Cited

U.S. PATENT DOCUMENTS

PP7,319 P * 9/1990 McGredy ..... Plt./102
PP8,839 P * 7/1994 Meilland ..... Plt./108
PP11,572 P * 10/2000 Evers ..... Plt./107

OTHER PUBLICATIONS

UPOV ROM GTITM Computer Databast, GTI Jouve Retrieval Software 2007/04 Citation for 'Jactoose'.*

* cited by examiner

*Primary Examiner*—Wendy C. Haas
(74) *Attorney, Agent, or Firm*—Klarquist Sparkman, LLP

(57) ABSTRACT

Shrub rose plant that exhibits ease of rooting as a soft or hardwood cutting; excellent disease resistance; vigorous spreading and arching habit of growth; and very glossy leather foliage.

1 Drawing Sheet

Genus and species: *Rosa hybrida.*
Variety denomination: 'JACtoose'.

ORIGIN OF THE INVENTION

The present invention relates to a new and distinct variety of a shrub rose plant named 'JACtoose' which was originated by me by crossing an unnamed red shrub rose plant (female parent, unpatented), parentage of female parent is 'MACminmo' (PP 7319)×unnamed seedling (not patented), with the variety 'TANotax' (male parent, PP 11572).

BACKGROUND OF THE INVENTION

The primary objective of this breeding was to produce a new shrub rose variety having the arching habit, disease resistance and own root vigor of the female unnamed seed parent combined with the disease resistance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Ease of rooting as a soft or hardwood cutting.
2. Excellent disease resistance.
3. Vigorous spreading and arching habit of growth.
4. Very glossy leather foliage.

Asexual reproduction of this new variety by cuttings, as performed at Wasco, Calif., shows that the foregoing characteristics and distinctions come true to form and are established and transmitted through succeeding propagations.

COMPARISON WITH PARENTS

The unnamed female seed parent differs in flower color (red for the female parent versus pink for 'JACtoose'). The male parent 'TANotax' differs in plant habit (spreading and arching for 'JACtoose' versus upright for 'TANotax').

COMPARISON WITH SIMILAR VARIETY

The most similar variety in habit is believed to be 'MACminmo' (PP7319). 'JACtoose' differs from 'MACminmo' in flower color (striped for 'MACminmo' versus pink for 'JACtoose').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with the Royal Horticultural society (London) Colour Chart® 2001, except where ordinary dictionary significance of color is indicated.

Parentage:

*Seed parent.*—Unnamed red shrub rose (not patented). Parentage of seed parent is 'MACminmo' (PP 7319)×unnamed seedling (unpatented).

*Pollen parent.*—'TANotax' (PP 11,572).

FLOWER

Observations made from January 2006 in June 2007 from plants commencing at two to three years of age grown in a garden environmental at Somis, Calif.

Blooming habit: Continuous.

Bud:

*Size.*—About 15 mm long and 11 mm in diameter when the petals start to unfurl.

*Form.*—The bud form is short, pointed ovoid.

*Color.*—When sepals first divide, bud color is Red Group 46B. When half blown, the upper sides of the petals are Red Group 46C and the lower sides of the petals are Red Group 46C.

*Sepals.*—Color: Upper surface: Green Group 138B. Lower surface: Yellow-Green Group 146C, overlain if in bright sun with Greyed-Purple Group 183B. Length: 12 mm. Width: 7 mm. Shape: Subulate. Surface texture: Hoary. There are three lightly appendaged sepals. There are two unappendaged sepals with hairy edges.

*Receptacle.*—Color: Yellow-Green Group 146B. Shape: Funnel. Size: Small, about 8 mm long×5 mm in diameter. Surface: Smooth.

*Peduncle.*—Length: Short, averaging about 25 mm. Surface: Glandular. Color: Yellow-Green Group 146C overlain, if in bright sun, with Greyed Purple Group 183B. Strength: Bending, slender.

Bloom:

*Size.*—Medium. Average open diameter is about 7–8 cm.

*Borne.*—Several together in clusters of 3–7 blooms having a flat shape.

*Stems.*—Strength: Strong. Average length is about 45 cm with a diameter of 7–8 mm.

*Form.*—When first open: Flat. Permanence: Retains its form to the end.

*Petalage.*—Number of petals under normal conditions: 8–10.

*Color.*—The upper sides of the petals are Red Group 46C. The reverse sides of the petals are Red Group 46C. The base of the petals has an approximately 5 mm×5 mm Yellow Group 9B color spot. The major color on the upper sides is Red Group 46C.

*Variegations.*—None observed.

*Discoloration.*—The general tonality at the end of the first day: No change. At the end of the third day: Little change. Further aging: At petal drop (day 4), the color changes to Red-Purple Group N57C.

*Fragrance.*—Slight, spicy.

Petals:

*Texture.*—Thick, leathery.

*Surface.*—Smooth.

*Shape.*—Obovate.

*Margin.*—Entire.

*Apex shape.*—Obcordate to obtuse.

*Base shape.*—Rounded.

*Form.*—Flat, tips slightly recurved.

*Arrangement.*—Imbricated.

*Petaloids.*—Number: None observed.

*Persistence.*—Petals drop off cleanly before drying.

*Lastingness.*—On the plant: Fair (about 4 days). As a cut flower: Fair (about 5 days).

Reproductive parts:

*Stamens.*—Number: 60–80. Length: 8–12 mm. Anthers: Length: 1–1.5 mm. Color: Yellow-Orange Group 17A. Arrangement: Regular around styles. Filaments: Color: Yellow-Orange Group 17C. Length: 7–11 mm. Pollen: Color: Greyed-Orange Group 170B.

*Pistils.*—Number: 40–60. Length: 4–6 mm. Styles: Color: Green-Yellow Group 1C. Length: 3–5 mm. Stigmas: Color: Yellow-Orange Group 15D. Length: 1 mm.

*Hips.*—Color: Begin Yellow-Green Group 146B, turning to Orange-Red Group 32A. Shape: Pear. Size: Length 18–22 mm width a diameter of 8–12 m.

PLANT

*Form.*—Blush, shrub

*Growth.*—Very vigorous, branching, spreading/sprawling.

*Age at maturity.*—Two years.

*Mature plant.*—Height: 3½ ft. Width: 4½ ft.

*Rootstock.*—Own root.

Foliage: Number of leaflets on normal mid-stem leaves: 5–7.

*Size.*—Medium. About 10–12 cm long×7–9 cm wide.

*Quantity.*—Normal.

*Color.*—New foliage: Upper side: Blend of Yellow-Green Group 146B and Greyed-Orange Group 176C. Lower side: Blend of Yellow-Green Group 146B and Greyed-Orange Group 176C. Old foliage: Upper side: Green Group 137A. Lower side: Green Group 138B.

Leaflets:

*Size.*—About 30–45 mm long×25–30 mm wide.

*Shape.*—Pointed oval.

*Base shape.*—Oblique.

*Apex shape.*—Cuspidate.

*Texture.*—Leathery, glossy.

*Edge.*—Serrated.

*Serrations.*—Single.

*Petiole.*—Color: Between Yellow-Green Group 144C and 144D.

*Petiole rachis.*—Color: Between Yellow-Green Group 144C and 144D. Underside: Prickles, few.

*Auricles.*—Subulate.

*Stipules.*—Length: 18–22 mm, bearded.

*Disease resistance.*—Resistance to mildew, rust and blackspot under normal growing conditions.

*Pest resistance.*—Not observed.

*Venation pattern.*—Reticulate.

Wood:

*New wood.*—Color: Greyed-Purple Group 183C. Bark: Smooth.

*Old wood.*—Color: Yellow-Green Group 146B. Bark: Smooth.

Prickles:

*Quantity.*—Ordinary, on main canes from base: 15–20 per 150 mm of cane. Ordinary, on laterals from main canes: 15–20 per 150 mm of cane.

*Form.*—Straight.

*Length.*—4–7 mm.

*Color when young.*—Greyed-Purple Group 183B.

*Color when mature.*—Greyed-Orange Group 177B.

Small prickles:

*Quantity.*—On main stalks: None observed. On laterals: None observed.

Water hardiness: Hardy to Zone 4.

I claim:

1. A new and distinct variety of rose plant of the shrub class, substantially as herein shown and described, characterized particularly by its ease of rooting as a soft or hardwood cutting; excellent disease resistance; vigorous spreading and arching habit of growth; and very glossy leather foliage.

* * * * *

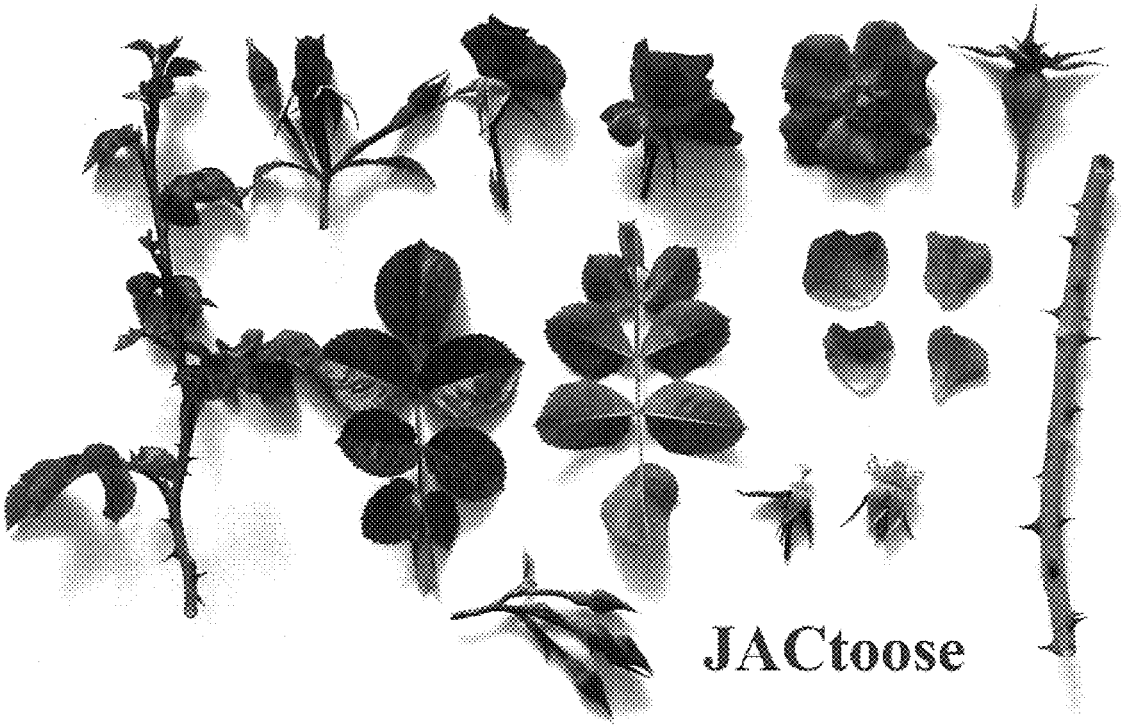
JACtoose

UNITED STATES PATENT AND TRADEMARK OFFICE

CERTIFICATE OF CORRECTION

PATENT NO. : PP19,131 P2
APPLICATION NO. : 11/824573
DATED : August 19, 2008
INVENTOR(S) : Keith W. Zary It is certified that error appears in the above-identified patent and that said Letters Patent is hereby corrected as shown below:

In the Specification:

Column 2, line 28, “Colour Chart®” should read -- Colour Chart© --

Column 3, line 2, “January 2006 in June 2007” should read -- January 2006 to June 2007 --

Column 3, line 5, “environmental” should read -- environment --

Column 4, line 9, “width” should read -- with --

Column 4, line 9, “8-12 m.” should read -- 8-12 mm. --

Column 4, line 13, “Blush” should read -- Bush --

Column 4, line 42, “Resistance” should read -- Resistant --

Column 4, line 62, “Water” should read -- Winter --

Signed and Sealed this
Fifteenth Day of March, 2011

David J. Kappos

David J. Kappos
*Director of the United States Patent and Trademark Office*